United States Patent
Ray et al.

(10) Patent No.: US 6,734,309 B1
(45) Date of Patent: May 11, 2004

(54) PROCESS FOR THE SYNTHESIS OF ISONICOTINIC ACID HYDRAZIDE

(75) Inventors: Subhash Chandra Ray, Dhanbad (IN); Lakshmi Narayan Nandi, Dhanbad (IN); Baldev Singh, Dhanbad (IN); Hiralal Prasad, Dhanbad (IN); Sumant Maharaj, Dhanbad (IN); Prodyot Kumar Sarkar, Dhanbad (IN); Pashupati Dutta, Dhanbad (IN); Shyam Kishore Roy, Dhanbad (IN); Satya Niketan Yadav, Dhanbad (IN); Anup Kumar Bandyopadhyay, Dhanbad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/393,372

(22) Filed: Mar. 20, 2003

(51) Int. Cl.⁷ ............................................. C07D 213/56
(52) U.S. Cl. ..................................... 546/316
(58) Field of Search ........................................ 546/316

(56) References Cited

U.S. PATENT DOCUMENTS 2,891,067 A    6/1959  Lal Mukherjee ............ 260/295

FOREIGN PATENT DOCUMENTS

DE    11 16 667    11/1961

OTHER PUBLICATIONS

Database CrossFire Beilstein 'Online! Beilstein Institut zur Forderung der Chemischen Wissenschaften, Frankfurt am Main, DE; Database accession No. Reaction ID: 329566 XP002237627. Abstract & Dzhumaulleva, S.A., et al Russ. J. Phys. Chem. vol. 67, No. 5 (1993) pp 976–977.

Database WPI Section Ch, Week 199627 Derwent Publications Ltd., London, GB; Class BO3, AN 1996–266597 XP002237628 & SU 1197396 (Orozhonikidze Chem Pharm Inst) (1995) col. 1, line 52–67, Ex. 2.

*Primary Examiner*—Patricia L. Morris
(74) *Attorney, Agent, or Firm*—Ladas & Parry

(57) ABSTRACT

The invention provides a process for the manufacture of isonicotinic acid hydrazide(INH) useful in the treatment of tuberculosis. The invention relates to the single step conversion of isonicotinamide by hydrazine hydrate to isonicotinic acid hydrazide (INH) of yield greater than 95% (w/w) and purity more than 99%.

8 Claims, No Drawings

PROCESS FOR THE SYNTHESIS OF ISONICOTINIC ACID HYDRAZIDE

FIELD OF THE INVENTION

The present invention relates to a process for the synthesis of isonicotinic acid hydrazide. More particularly, the present invention relates to a process for the synthesis of isonicotinic acid hydrazide(INH) from isonicotinamide. Isonicotinic acid hydrazide (INH) is used in the treatment of tuberculosis.

BACKGROUND OF THE INVENTION

Pyridine carboxylic acid hydrazide is prepared by the reaction of an ester or an acid chloride with hydrazine or substituted hydrazines. For the preparation of unsubstituted pyridine carbohydrazide, reaction between an ester and hydrazine gives good yield. If the acid chloride is used, a dipyridoyl hydrazine may be formed, but replacement of active halogen in 2- & 4-hydrazides is difficult.

Acid hydrazides are generally prepared by the reaction of hydrazine with an ester or an acyl chloride. Amides and acids can also be converted to the respective hydrazides by treatment with hydrazine hydrate, but, in general, amides appears to be more sluggish than ester in the reaction with hydrazine hydrate. The overall yield of acid hydrazide is not satisfactory.

Reference is made to Indian Patent No. 100112 wherein the process steps comprise of oxidation of 4-picoline by nitric acid to isonicotinic acid; esterification of isonicotinic acid and treatment of the resulting ester with hydrazine hydrate. The drawback of the process is that it causes corrosion of the reactor and separation of the ester is a very cumbersome.

Reference is also be made to Indian Patent No: 107934 wherein the process steps comprises of oxidation of 4-picoline by potassium permanganate to isonicotinic acid; esterification of isonicotinic acid and treatment of resulting ester by hydrazine hydrate. The drawback of the process is that the overall yield is very poor and separation of ester is very difficult.

Prior art search for synthesis of isonicotinic acid hydrazide from isoniconitinamide was made based on literature survey and patent databases, which did not yield any relevant references.

OBJECTS OF THE INVENTION

The main object of the invention is to provide a process for the conversion of isonicotinamide to isonicotinic acid hydrazide (INH) by hydrazine hydrate which obviates the drawbacks as detailed above.

Another object of the invention is to provide a process for the conversion of isonicotinamide to isonicotinic acid hydrazide (INH) by hydrazine hydrate.

Yet another object of the invention is to convert isonicotinamide to obtain yield greater than 95% (w/w) of isonicotinic acid hydrazide 99% purity.

Still another object of the invention is to provide a simple and single step process avoiding harmful chemicals and saving energy.

SUMMARY OF THE INVENTION

The invention provides a process for the manufacture of isonicotinic acid hydrazide(INH) useful in the treatment of tuberculosis. The invention relates to the single step conversion of isonicotinamide by hydrazine hydrate to isonicotinic acid hydrazide(INH) of yield greater than 95%(w/w) and purity more than 99%.

Accordingly the present invention provides a process for the preparation of isonicotinic acid hydrazide which comprises dissolving isonicotinamide in C1 to C3 alcohol, adding hydrazine hydrate to the isonicotinamide solution, refluxing the resultant mixture and distilling off alcohol to obtain isonicotinic acid hydrazide.

In one embodiment of the invention, the reaction is carried out in a single step.

In another embodiment of the invention, the isonicotinamide to alcohol ratio is in the range of 1:1 to 1:8.

In yet another embodiment of the invention, the hydrazine hydrate is added to the solution of isonicotinamide in a ratio in the range of 0.4 to 2 of hydrazine hydrate to isonicotinamide.

In yet another embodiment of the invention, the mixture of hydrazine hydrate and isonicotinamide solution is refluxed at a temperature in the range of 100 to 120° C. for a time period in the range of 3–5 hours.

In another embodiment of the invention the yield of isonicotinic acid hydrazide is greater than 95% (w/w) when hydrazine hydrate (100%) is used.

In another embodiment of the invention hydrazine hydrate used is in ratio in the range of 0.7 to 1.1 to obtain yield of isonicotinic acid hydrazide(INH) greater than 97% (w/w).

In another embodiment of the invention the purity of isonicotinic acid hydrazide(INH) obtained is greater than 99%.

DETAILED DESCRIPTION OF THE INVENTION

The novelty of the present invention resides in converting an amide (isonicotinamide) to isonicotinic acid hydrazide (INH) in a single step reaction in comparison to multi-step prior art processes and recovering the alcohol added after the reaction in full.

The above said novelty and usefulness has been achieved by the non-obvious single inventive step of the process of the present invention.

The following examples are given by way of illustration of the present invention and should not be construed to limit the scope of the present invention.

EXAMPLE-1

9.9918 gms of isonicotinamide was dissolved in 77.97 gms of absolute alcohol and 10.1 gms of hydrazine hydrate (100%) was added to it. The reaction mixture was refluxed in glycerine bath for 4 hours at 115 degree Celsius; after which alcohol was distilled off and solid mass, Isonicotinic acid hydrazide (INH) was taken out in hot condition Recovered Isonicotinic acid hydrazide was 9.727 gms i.e. 97.34 wt % and the melting point obtained was 170° C. against 169.9° C. actual.

EXAMPLE-2

19.3989 gins of isonicotinamide was dissolved in 39.488 gms of methyl alcohol and 14.14 gms of hydrazine hydrate (100%) was added to it. The reaction mixture was refluxed in glycerine bath for 4 hours at 110 degree Celsius; after which alcohol was distilled off and solid mass, Isonicotinic acid hydrazide (INH) was taken out in hot condition. Recovered Isonicotinic acid hydrazide was 19.3 gms i.e. 99.49 wt % and the melting point obtained was 169.9° C. against 170° C. actual.

EXAMPLE-3

24.99 gms of isonicotinamide was dissolved in 39.48 gms of methyl alcohol and 20.20 gms of hydrazine hydrate (100%) was added to it. The reaction mixture was refluxed in glycerine bath for 4 hours at 110 degree Celsius; after which alcohol was distilled off and solid mass, Isonicotinic acid hydrazide(INH) was taken out in hot condition. Recovered Isonicotinic acid hydrazide was 24.0 gms i.e. 96.03 wt % and the melting point obtained was 169.9° C. against 170° C. actual.

The main advantages of the present invention are:
1. It is a simple and singe step process, avoiding handling of harmful chemicals and saving energy.
2. Purity of the product achieved was more than 99% as evidenced by melting point determination and through FTIR Spectroscopy.

We claim:
1. A process for the preparation of isonicotinic acid hydrazide which comprises dissolving isonicotinamide in C1 to C3 alcohol, adding hydrazine hydrate to the isonicotinamide solution, refluxing the resultant mixture and distilling off alcohol to obtain isonicotinic acid hydrazide.

2. A process as claimed in claim 1 wherein the reaction is carried out in a single step.

3. A process as claimed in claim 1 wherein the the isonicotinamide to alcohol ratio is in the range of 1:1 to 1:8.

4. A process as claimed in claim 1 wherein the hydrazine hydrate is added to the solution of isonicotinamide in a ratio in the range of 0.4 to 2 of hydrazine hydrate to isonicotinamide.

5. A process as claimed in claim 1 wherein the mixture of hydrazine hydrate and isonicotinamide solution is refluxed at a temperature in the range of 100 to 120° C. for a time period in the range of 3–5 hours.

6. A process as claimed in claim 1 wherein the yield of isonicotinic acid hydrazide is greater than 95% (w/w) when hydrazine hydrate (100%) is used.

7. A process as claimed in claim 1 wherein the hydrazine hydrate used is in a ratio in the range of 0.7 to 1.1 to obtain yield of isonicotinic acid hydrazide(INH) greater than 97% (w/w).

8. A process as claimed in claim 1 wherein the purity of isonicotinic acid hydrazide(INH) obtained is greater than 99%.

* * * * *